United States Patent
Kirkwold et al.

(10) Patent No.: US 9,675,719 B2
(45) Date of Patent: Jun. 13, 2017

(54) STAGING CONTROL FOR AN EVAPORATIVE MEDIA SYSTEM

(71) Applicant: DRI-STEEM Corporation, Eden Prairie, MN (US)

(72) Inventors: Mark Allen Kirkwold, Shakopee, MN (US); Cole K. Farley, Long Lake, MN (US); James M. Lundgreen, Lakeville, MN (US)

(73) Assignee: Dri-Steem Corporation, Eden Prairie, MN (US)

( * ) Notice: Subject to any disclaimer, the term of this patent is extended or adjusted under 35 U.S.C. 154(b) by 331 days.

(21) Appl. No.: 14/598,880

(22) Filed: Jan. 16, 2015

(65) Prior Publication Data

US 2015/0204553 A1    Jul. 23, 2015

Related U.S. Application Data

(60) Provisional application No. 61/928,784, filed on Jan. 17, 2014, provisional application No. 61/928,740, (Continued)

(51) Int. Cl.
*F24F 5/00* (2006.01)
*F28C 3/08* (2006.01)
(Continued)

(52) U.S. Cl.
CPC ............ *A61L 2/10* (2013.01); *B01F 3/04021* (2013.01); *B01F 3/04078* (2013.01); (Continued)

(58) Field of Classification Search
CPC .. F24F 5/0035; F24F 6/02; F24F 6/043; F24F 2001/0088; F25D 7/00; F28C 3/08; B01F 3/04021; B01F 3/04078; Y02B 30/545
(Continued)

(56) References Cited

U.S. PATENT DOCUMENTS 6,513,339 B1    2/2003  Kopko
7,165,410 B2    1/2007  Carr et al.
(Continued)

FOREIGN PATENT DOCUMENTS

WO    WO 01/79771 A1      10/2001
WO    WO 2007/055838 A2    5/2007

*Primary Examiner* — Marc Norman
(74) *Attorney, Agent, or Firm* — Merchant & Gould P.C.

(57) ABSTRACT

A staging control process for an evaporative media cooling system having a plurality of media stages is disclosed. In one step, a leaving air dry bulb temperature setpoint for air exiting the evaporative media cooling system is received or defined. In one aspect, an expected media exit dry bulb temperature is calculated for each media stage based on a dry bulb temperature and a wet bulb temperature of air entering the media cooling system and based on a measured or assigned condition of the media. In another aspect, an estimated combined leaving dry bulb temperature is calculated for different combinations of activated and deactivated media stages. Once the estimated leaving temperature is known, the method can then activate the media stage(s) associated with the combination that has an estimated combined leaving dry bulb temperature that is nearest to but less than the leaving air dry bulb temperature setpoint.

20 Claims, 4 Drawing Sheets

Related U.S. Application Data filed on Jan. 17, 2014, provisional application No. 61/928,764, filed on Jan. 17, 2014, provisional application No. 61/928,775, filed on Jan. 17, 2014, provisional application No. 61/928,800, filed on Jan. 17, 2014.

(51) Int. Cl.

| | | |
|---|---|---|
| A61L 2/10 | (2006.01) | |
| B01F 3/04 | (2006.01) | |
| F25B 39/02 | (2006.01) | |
| F25D 7/00 | (2006.01) | |
| G05D 9/12 | (2006.01) | |
| F24F 6/04 | (2006.01) | |
| F24F 1/00 | (2011.01) | |

(52) U.S. Cl.
CPC ........ *B01F 3/04085* (2013.01); *F24F 5/0035* (2013.01); *F24F 6/043* (2013.01); *F25B 39/02* (2013.01); *F25B 39/028* (2013.01); *F25D 7/00* (2013.01); *F28C 3/08* (2013.01); *G05D 9/12* (2013.01); *F24F 2001/0088* (2013.01); *Y02B 30/545* (2013.01); *Y10T 137/0318* (2015.04); *Y10T 137/7303* (2015.04)

(58) Field of Classification Search
USPC ........................................ 62/121, 171, 259.4
See application file for complete search history.

(56) References Cited

U.S. PATENT DOCUMENTS

| | | | |
|---|---|---|---|
| 7,712,300 | B2 | 5/2010 | Bevilacqua et al. |
| 7,765,827 | B2 | 8/2010 | Schlom et al. |
| 8,496,732 | B2 | 7/2013 | Culp et al. |
| 2004/0093882 | A1 | 5/2004 | Sangwan et al. |
| 2007/0101746 | A1 | 5/2007 | Schlom et al. |
| 2011/0030552 | A1 | 2/2011 | Fong et al. |
| 2012/0118148 | A1 | 5/2012 | Culp et al. |
| 2012/0118155 | A1 | 5/2012 | Claridge et al. |
| 2013/0333407 | A1 | 12/2013 | Jarvis |
| 2014/0190198 | A1* | 7/2014 | Slessman ........... H05K 7/20836 62/314 |
| 2015/0204552 | A1 | 7/2015 | Kirkwold et al. |
| 2015/0204554 | A1 | 7/2015 | Farley et al. |
| 2015/0204588 | A1 | 7/2015 | Lundgreen et al. |
| 2015/0205305 | A1 | 7/2015 | Kirkwold et al. |
| 2015/0260419 | A1 | 9/2015 | Muenzberg et al. |

\* cited by examiner

STAGING CONTROL FOR AN EVAPORATIVE MEDIA SYSTEM

CROSS-REFERENCE TO RELATED APPLICATIONS

This application claims priority to U.S. Application Ser. No. 61/928,740, filed on Jan. 17, 2014, entitled "Evaporative Cycles of Concentration Control," the entirety of which is incorporated by reference herein. This application also claims priority to U.S. Application Ser. No. 61/928,764, filed on Jan. 17, 2014, entitled "Circulation and Drain System," the entirety of which is incorporated by reference herein. This application claims priority to U.S. Application Ser. No. 61/928,775 filed on Jan. 17, 2014, entitled "Staging Control for an Evaporative Media System," the entirety of which is incorporated by reference herein. This application also claims priority to U.S. Application Ser. No. 61/928,784, filed on Jan. 17, 2014, entitled "Staging Control for an Evaporative Media System," the entirety of which is incorporated by reference herein. This application also claims priority to U.S. Application Ser. No. 61/928,800, filed on Jan. 17, 2014, entitled "Staged Dry Out Control for Evaporative Media Systems," the entirety of which is incorporated by reference herein.

BACKGROUND

Evaporative media systems, for example direct evaporative coolers, are frequently used in commercial and industrial HVAC systems, including applications for data centers and power plant turbine inlet cooling. Evaporative media systems consume less energy than conventional cooling equipment and are increasingly being used to supplement and occasionally replace conventional cooling equipment. In operation, evaporative media systems use the enthalpy of vaporization of water as a means to cool and humidify air. Typically, this is accomplished by flowing air directly through a media wetted with water. As air passes through the wetted media, water evaporates by taking energy from the air to vaporize the water. Accordingly, the air temperature exiting the wetted media is reduced and the humidity is increased while the energy or enthalpy of the exiting air remains the same as the entering air. This type of a process is often referred to as adiabatic cooling.

It is desirable to not cycle a wetted media stage in an evaporative media system more often than absolutely necessary. This is because as the water dries out, any solids in the water will be deposited on the media. This scale build-up is a significant wear-out mechanism for wetted media. Even so, many feedback based control schemes for activating or staging the media stages to meet an output demand tend to cycle the media stages excessively. This circumstance exists because many feedback based control schemes are effectively always performing an "experiment" on the system and adjusting the output accordingly. For example, if the output is too high, the controller would adjust the command signal to lower the output, if it is too low, it would act to increase the output. Since the output of an evaporative media system needs to be discreet (i.e. each media stage is either dry or completely wet) in order to minimize scale build-up, the control system cannot track this analog signal. As a consequence the analog signal will go up until the entire system or a stage of the system is turned on. If this activation causes an overshoot of the setpoint, the analog signal will decrease until it is turned off, and the cycle repeats.

If the system is a single-stage unit, the addition of the some hysteresis to the control loop may be enough to stabilize the output. However, if the unit has more output levels than one, satisfactory control becomes more difficult. For example, a 1/3, 2/3 unit has two stages that can be on or off with one stage (the 2/3) being twice the size of the other (the 1/3). Such a unit has four output states: off, 1/3, 2/3 or 3/3. Improvements in staging control for multiple stage evaporative cooling systems are desired.

SUMMARY

A staging control process and control system for an evaporative media cooling system having a plurality of media stages is disclosed. In one aspect, the staging control process can include the step of defining a plurality of allowed unit staging configurations, wherein each configuration represents a combination of activated and deactivated media stages that is different from all other allowed unit staging configurations. In one embodiment, a leaving air dry bulb temperature setpoint for air exiting the evaporative media cooling system is defined in a controller associated with the evaporative media system while in another embodiment, the temperature setpoint is received from a controller associated with the air handling system. One step of the process can include calculating an expected media exit dry bulb temperature for each media stage based on a dry bulb temperature and a wet bulb temperature of air entering the media cooling system and based on a measured or assigned condition of the media. The condition of the media can be a constant value, a measured value, an input value, a calculated value, or combinations thereof.

In one step, an estimated combined leaving dry bulb temperature for each allowed unit staging configuration is calculated. In one embodiment, each deactivated media stage in the configuration is assigned a leaving dry bulb temperature equal to the entering air dry bulb temperature and each activated media stage is assigned a leaving dry bulb temperature equal to the expected media exit dry bulb temperature. In another step, the media stages are activated that are associated with the allowed unit staging configuration having an estimated combined leaving dry bulb temperature that is nearest to but less than the leaving air dry bulb temperature setpoint.

DESCRIPTION OF THE DRAWINGS

Non-limiting and non-exhaustive embodiments are described with reference to the following figures, which are not necessarily drawn to scale, wherein like reference numerals refer to like parts throughout the various views unless otherwise specified.

DETAILED DESCRIPTION

Figure 1:
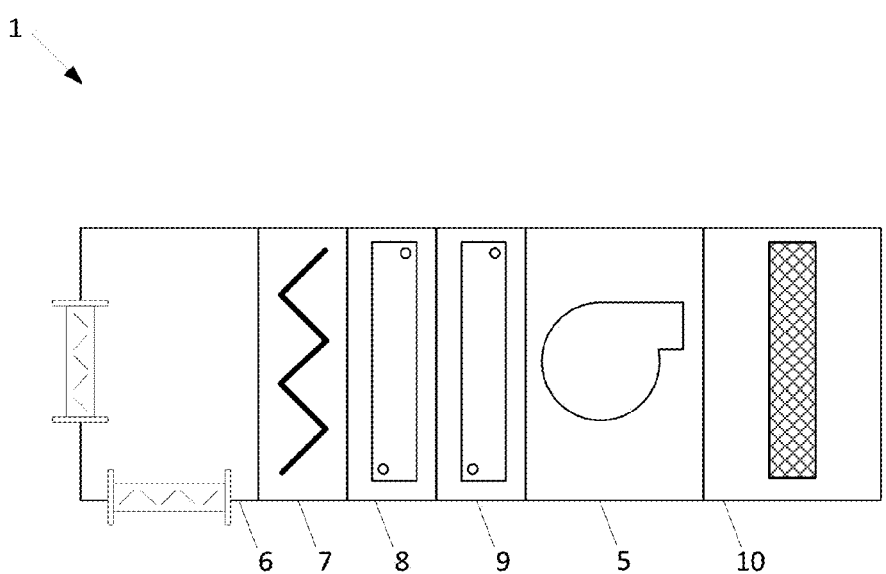
FIG. 1 is a schematic view of an air handling system having features that are examples of aspects in accordance with the principles of the present disclosure.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

General Evaporative Media System Description

Figure 2:
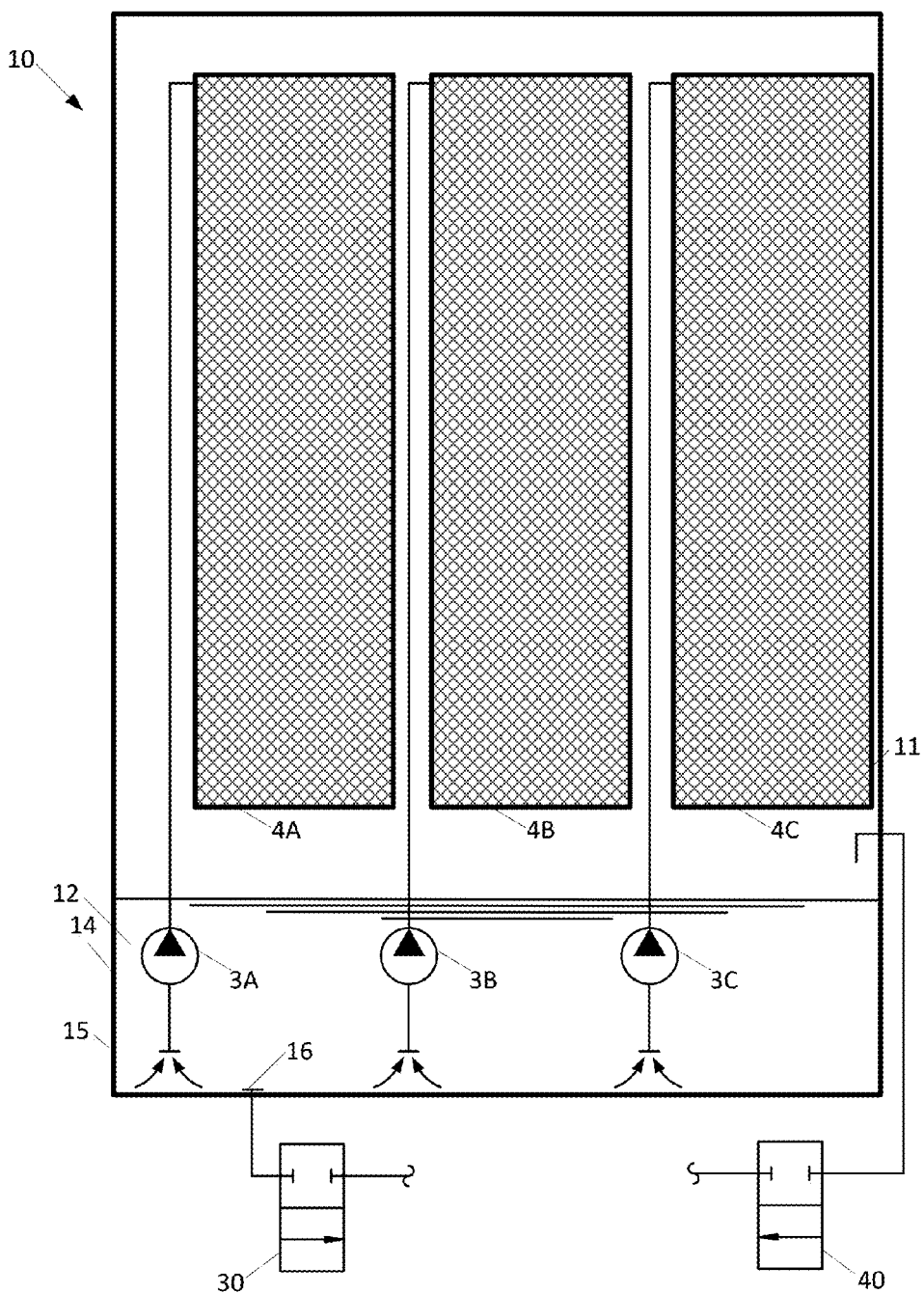
FIG. 2 is a schematic view of an evaporative media system having features that are examples of aspects in accordance with the principles of the present disclosure, the evaporative media system being usable in the air handling system shown in FIG. 1.
Figure 3:
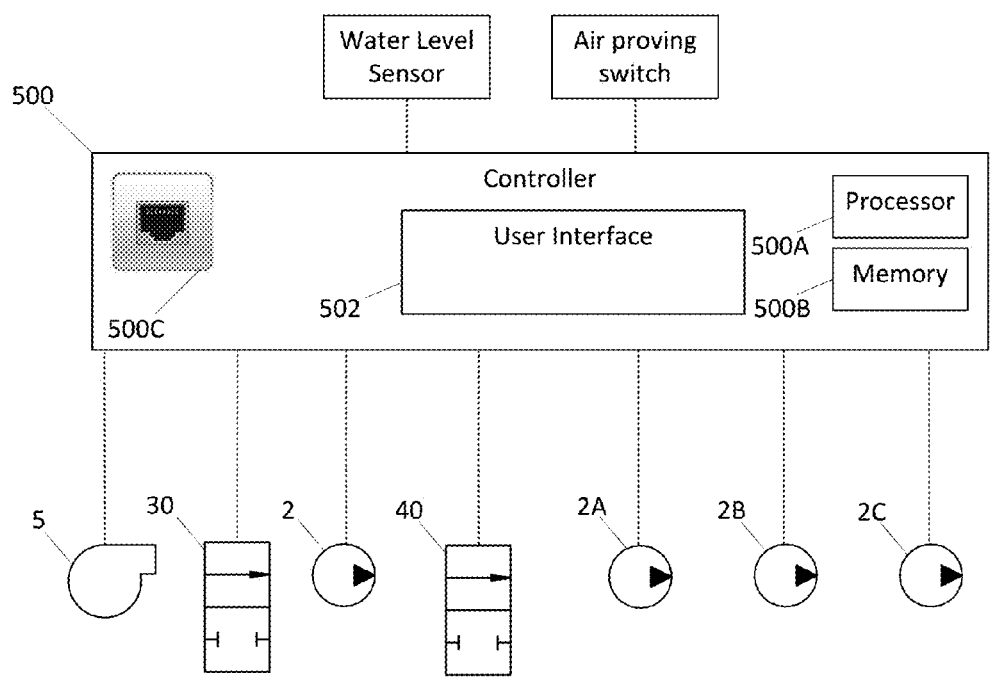
FIG. 3 is a schematic view of a control system usable with the evaporative media system and air handling unit shown in FIG. 1.

Referring to FIG. 1, an air handling system 1 comprising an evaporative media system 10 is shown. FIG. 2 shows the evaporative media system 10 in additional detail. As shown, the air handling unit may be additionally provided with a supply fan 5, a damper section 6, a filter 7, a heating coil 8, and a cooling coil 9. It should be understood that various other components and alternative configurations may be applied to air handling system 1 without departing from the concepts disclosed herein. In operation, the supply fan 5 draws air through the evaporative media system 10 to result in adiabatically cooled air when the evaporative media system 10 is activated.

In one aspect, the evaporative media system 10 includes an evaporator tank 14 having a sidewall 15 and a bottom side 17 that together define an interior volume 11 for holding a fluid 12, such as water. The sidewall 15 may have various cross-sectional shapes as dictated by the requirements of the evaporator and air handling unit, for example square, rectangular, and circular cross-sectional shapes. The bottom side 17 may also be provided with various shapes to accommodate the perimeter defined by the sidewall 15.

The storage tank 14 may be provided with a drain opening 16 located in one of the bottom side 17 and the sidewall 15. In the particular embodiment shown, the drain opening 16 is provided at the bottom side 17 of the tank 14. In one aspect, a drain valve 30 is provided to selectively drain water from the tank 14 while a fill valve 40 is provided to selectively add water to the tank 14. The drain and fill valves 30, 40 may be provided as automatic control valves operated by a controller, such as electronic controller 500 discussed below.

As presented, evaporative media system 10 also includes a plurality of media stages 4A, 4B, 4C through which air is drawn via the operation of fan 5. Although three media stages are shown, it should be appreciated that the evaporative media system 10 may include fewer or more media stages without departing from the concepts disclosed herein. Furthermore, each media stage may include multiple sections of media. As shown, each media section 4A, 4B, 4C is separated from the other by a gap, or alternatively a barrier, to prevent moisture from communicating from one section to the other. This configuration allows for an individual media section to be dry out without being subjected to wicking moisture from an adjacent section.

Each of the media stages 4A, 4B, 4C is shown as being provided with an associated distribution pump 3A, 3B, 3C. While there is a one-to-one relationship shown between the media stages 4A, 4B, 4C and the pumps 3A, 3B, 3C, is should be understood that more than one media stage can be served by a single pump, with or without individual valves, to result in a larger media stage consisting of multiple media sub stages.

In operation, when a pump 3A, 3B, 3C is activated (e.g. turned on or modulated to a speed greater than zero), the associated media stage 4A, 4B, 4C is wetted with fluid 12. When a media stage 4A, 4B, 4C is being actively wetted with water, for example when the associated pump 3A, 3B, 3C is in operation, that media stage 4A, 4B, 4C can be referred to as being activated. Likewise, when a media stage 4A, 4B, 4C is not being actively wetted with water, for example when the associated pump 3A, 3B, 3C is shut off and not in operation, that media stage 4A, 4B, 4C can be referred to as being deactivated.

Control System

Referring to FIG. 2, the evaporative media system may also include an electronic controller 500. The electronic controller 500 is schematically shown as including a processor 500A and a non-transient storage medium or memory 500B, such as RAM, flash drive or a hard drive. Memory 500B is for storing executable code, the operating parameters, and the input from the operator user interface 502 while processor 500A is for executing the code. The electronic controller is also shown as including a transmitting/receiving port 500C, such as an Ethernet port for two-way communication with a related WAN/LAN or to another controller associated with the automation system. A user interface 502 may be provided to activate and deactivate the system, allow a user to manipulate certain settings or inputs to the controller 500, and to view information about the system operation.

The electronic controller 500 typically includes at least some form of memory 500B. Examples of memory 500B include computer readable media. Computer readable media includes any available media that can be accessed by the processor 500A. By way of example, computer readable media include computer readable storage media and computer readable communication media.

Computer readable storage media includes volatile and nonvolatile, removable and non-removable media implemented in any device configured to store information such as computer readable instructions, data structures, program modules or other data. Computer readable storage media includes, but is not limited to, random access memory, read only memory, electrically erasable programmable read only memory, flash memory or other memory technology, compact disc read only memory, digital versatile disks or other optical storage, magnetic cassettes, magnetic tape, magnetic disk storage or other magnetic storage devices, or any other medium that can be used to store the desired information and that can be accessed by the processor 500A.

Computer readable communication media typically embodies computer readable instructions, data structures, program modules or other data in a modulated data signal such as a carrier wave or other transport mechanism and includes any information delivery media. The term "modulated data signal" refers to a signal that has one or more of its characteristics set or changed in such a manner as to encode information in the signal. By way of example, computer readable communication media includes wired media such as a wired network or direct-wired connection, and wireless media such as acoustic, radio frequency, infrared, and other wireless media. Combinations of any of the above are also included within the scope of computer readable media.

Electronic controller 500 is also shown as having a number of inputs/outputs that may be used for implementing the below described operational modes of the evaporative media system 10 and/or the air handling system 1. For example, electronic controller 500 provides outputs for commanding individual evaporator stage pumps 3A, 3B, 3C, an output for controlling a tank fill valve 40, and an output for controlling a tank drain valve 30. Status inputs can be provided for each of the aforementioned control components as well. Additionally, inputs for entering and leaving air temperature and humidity, outdoor air temperature and humidity, tank water level, tank water temperature (which can serve as a proxy for entering and leaving air wet bulb temperatures), and an airflow switch (or a fan status input signal) may be provided as well. The controller 500 can also include the necessary inputs and outputs for desirable operation of the remaining components of the air handling system 1, for example, inputs and outputs to operate the fan 5, damper section 6, and the coils 8, 9.

In one aspect, the controller 500 may be programmed to execute a staging control process whereby selected media stages are activated to meet a leaving air temperature setpoint, as explained in the following paragraphs.

Staging Control Process Description

Figure 4:
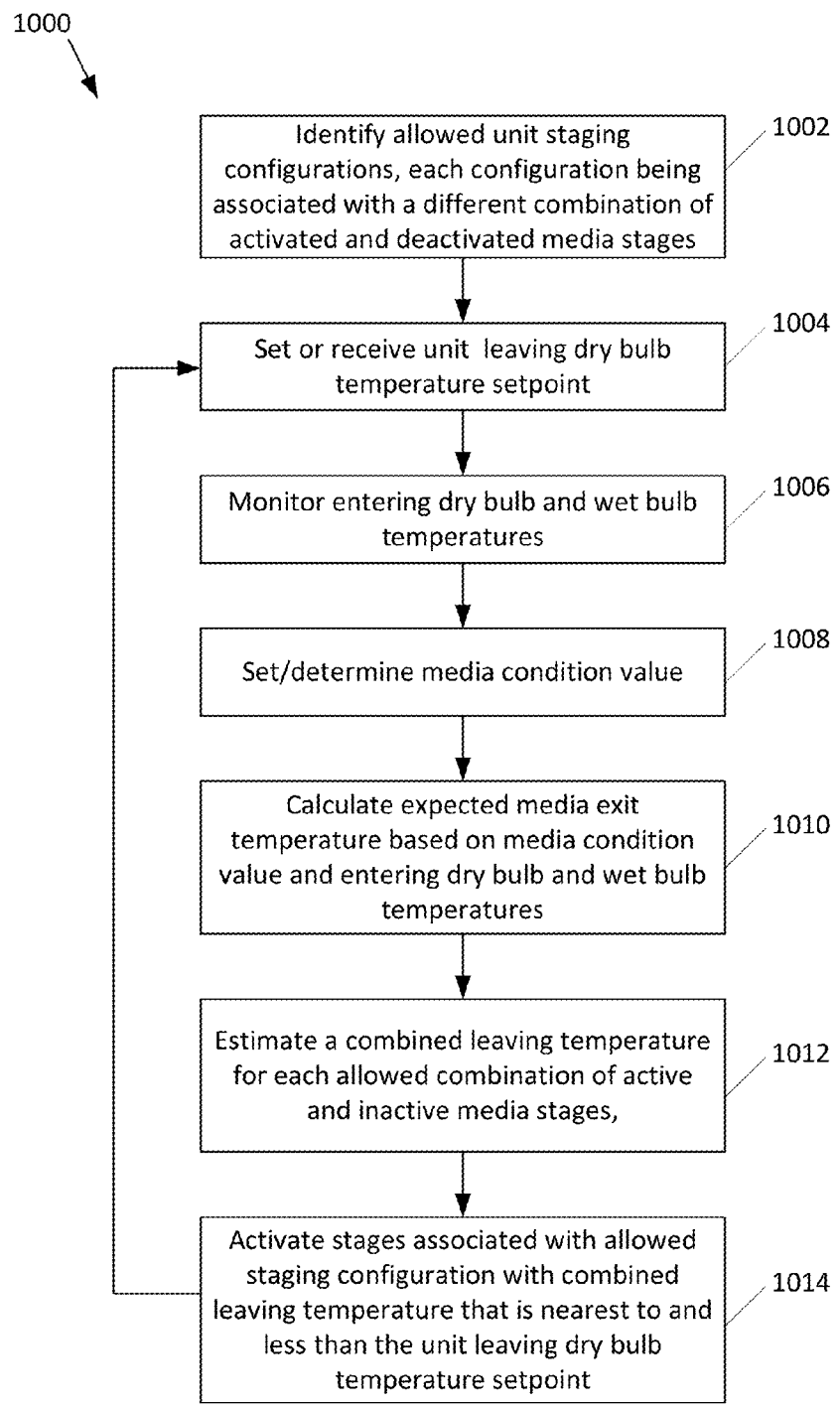
FIG. 4 is a flow diagram for a staging control process usable with the air handling system and the evaporative media system shown in FIG. 1, and executable by the control system shown in FIG. 3.

Referring to FIG. 4, an example of a staging control process 1000 in accordance with the disclosure is presented. It is noted that although the figures diagrammatically show steps in a particular order, the described procedures are not necessarily intended to be limited to being performed in the shown order. Rather at least some of the shown steps may be performed in an overlapping manner, in a different order and/or simultaneously. Also, the process shown in FIG. 4 is exemplary in nature and other steps or combinations of steps may be incorporated or altered without departing from the central concepts disclosed herein.

In one aspect, staging control process 1000 is for controlling the staging of the media stages of an evaporative media cooling system. Generally, the staging control process 1000 helps to ensure that the determination of which media stage(s) are activated will be the best combination suited to the current system load or demand. Such an approach additionally prevents unnecessary cycling of a wetted media stage more often than absolutely necessary which helps to prevent or reduce scale build-up, a significant wear-out mechanism for wetted media.

In a step 1004, the staging control process defines a plurality of allowed unit staging configurations, wherein each configuration represents a combination of activated and deactivated media stages that is different from all other allowed unit staging configurations. For example, for a evaporative media system having three stages, 4A, 4B, 4C, a potential set of allowed unit staging configurations could be: (1) stage 4A activated with stages 4B and 4C deactivated; (2) stage 4B activated with stages 4A and 4C deactivated; (3) stage 4C activated with stages 4A and 4B deactivated; (4) stages 4A and 4B activated with stage 4C deactivated; (5) stages 4B and 4C activated with stage 4A deactivated; (6) stages 4A and 4C activated with stage 4B deactivated; and (7) stages 4A, 4B, and 4C activated. Where some configurations are redundant or undesirable, those configurations can be excluded from the allowed configurations.

Additionally, the process 1000 can be configured so that the explicit definition of allowed configurations is not needed by simply performing calculations for every possible combination at step 1012 and selectively activating/deactivating media stages based on the comparison of each possible combination at step 1014.

In a step 1004, a leaving air dry bulb temperature setpoint for air exiting the evaporative media cooling system is defined. In one embodiment, this setpoint can be defined or preconfigured in a controller associated with the evaporative media system. In one embodiment, this setpoint can be received from another controller, such as a controller associated with the operation of the air handling system. In another step 1006, the dry and wet bulb temperatures for the air entering the evaporative media system are monitored, which can be accomplished through an air handling unit controller and/or the evaporative media system controller via temperature sensors.

In a step 1008, a media condition value is set or determined. The media condition is a value corresponding to the fraction of the temperature difference between the entering air wet and dry bulb temperature that will be imparted to the air passing through the media. Accordingly, the media condition value can be utilized to predict the leaving air dry bulb temperature through the media stage(s). The media condition value can be a constant value, a measured value, an input value, a calculated value, or combinations thereof. Where a calculated value is used, operating parameters of the system may be utilized to accomplish the calculation, for example by utilizing system run time and water condition factors. Measuring the media condition can also be accomplished through the use of sensed system operating parameters. For example, the measurement can be performed by measuring the actual temperature drop across the media while it is running and dividing this by the potential temperature drop (which is the incoming dry bulb temperature minus the incoming wet bulb temperature).

If the unit is instrumented to allow measurement of the media condition to be made continuously there are some additional benefits. For example, real-time monitoring of media condition can be accomplished which could also be used to signal maintenance or schedule replacement of the media. The measured condition can also be used to determine actual dry out times. When the media is being intentionally dried out (e.g. to discourage algae growth) the actual dry-out time needed is a strong function of operating conditions. Instead of drying the media for the worst-case time, the drying profile can be measured during the dry-out cycle so that the media can be dried for as long as necessary, but not longer than necessary. Fault detection can also be accomplished. For example, a condition of when the valves and/or pumps are stuck in an on or off state may be detected by noting that the media is not active when it should be or is active when it should not be.

In a step 1010, the expected media exit temperature can be calculated for each media stage based on: (1) the entering air dry bulb temperature; (2) the entering air wet bulb temperature; and the (3) measured or assigned media condition value. This calculation can be performed by subtracting the wet bulb entering air temperature from the dry bulb entering air temperature and multiplying the difference by the media condition value. In a step 1012, an estimated combined leaving dry bulb temperature for each allowed unit staging configuration is calculated, or in the case where such configurations are not somehow defined, for all possible staging combinations. In one embodiment, each deactivated media stage in the configuration is assigned a leaving dry bulb temperature equal to the entering air dry bulb temperature and each activated media stage is assigned a leaving dry bulb temperature equal to the expected media exit dry bulb temperature. Where different air flow rates are anticipated through one or more of the media stages, the combined leaving temperature can be appropriately weighted.

In another step 1014, the media stages are activated that are associated with the allowed unit staging configuration that most closely matches the temperature setpoint. For example, the configuration that has an estimated combined leaving dry bulb temperature that is nearest to but less than the leaving air dry bulb temperature setpoint could be selected. The process moves back to step 1004 where the staging of the evaporative media system can be continually adjusted to account for any changes in the entering air conditions and/or the leaving temperature setpoint.

Example Operation

In one example of the execution of staging control process 1000, a two stage unit is controlled in which the unit has a total output capacity with both stages on, a one third output capacity with only the first stage on; and a two thirds output capacity with only the second stage on. The unit has a total output capacity of zero when both stages are off.

At a step 1002, the allowed unit staging configurations are identified in the controller as: (1) a 0/3 configuration in which no stages are activated; (2) a 1/3 configuration in which only the first stage is activated; (3) a 2/3 configuration in which only the first stage is activated; and (4) a 3/3 configuration in which both of the stages are activated.

For the purpose of the example, a leaving air temperature setpoint ($T_{sp}$) of 75° F. is selected or received at step 1004; an entering air dry bulb temperature is measured ($T_{db}$) to be 95° F. and an entering air wet bulb temperature ($T_{wb}$) is measured to be 55° F. at step 1006; and a media condition (M) of 0.85 is chosen, measured, or calculated at step 1008.

At step 1010, the expected media exit temperature ($T_{ex}$) can then be calculated for the media sections with the following formula:

$$T_{ex} = T_{db} - M^*(T_{db} - T_{wb})$$

Utilizing the parameters identified for the example, the expected air temperature for an activated media section calculates as follows:

$$T_{ex} = 95 - 0.85^*(95-55) = 61° \text{ F.}$$

At step 1012, the combined leaving temperature $T_{x/3}$ for the entire unit can then be calculated. For the purpose of the example, the air flow through the first stage is assumed to be one third of the total air flow through the unit while the air flow through the second stage is assumed to be two thirds of the total air flow through the unit, regardless of whether the stages are active or inactive. One skilled in the art will recognize that measured airflow rates or other means may be utilized when weighting the relative capacity contribution of each stage in calculating a leaving temperature. On this basis, the combined leaving temperature $T_{x/3}$ for each configuration can be calculated, as follows:

0/3 Configuration: $T_{0/3} = 1/3^*(T_{db}) + 2/3^*(T_{db}) = 1/3^*(95) + 2/3^*(95) = 95°$ F.

1/3 Configuration: $T_{1/3} = 1/3^*(T_{ex}) + 2/3^*(T_{db}) = 1/3^*(61) + 2/3^*(95) = 83.7°$ F.

2/3 Configuration: $T_{2/3} = 1/3^*(T_{db}) + 2/3^*(T_{ex}) = 1/3^*(95) + 2/3^*(61) = 72.3°$ F.

3/3 Configuration: $T_{3/3} = 1/3^*(T_{ex}) + 2/3^*(T_{ex}) = 1/3^*(61) + 2/3^*(61) = 61°$ F.

At a step 1014, the configuration that most closely approximates the leaving dry bulb temperature setpoint $T_{sp}$ can then be selected. For example, the 2/3 configuration could be selected as an optimum configuration since the leaving temperature $T_{2/3}$ is the closest to the temperature setpoint $T_{sp}$, but is also lower than the setpoint, thus ensuring that the setpoint $T_{sp}$ can be reached. Once this selection is made, the system can activate the second stage and ensure that the second stage is deactivated. As noted above, the control can return to step 1004 for continued monitoring of the setpoint and the entering air conditions such that a new configuration can be implemented should conditions warrant.

The above described approach can be utilized for any number of stages, and is therefore not only limited to a system with two stages. For example, three separate stages can be used having the same or different capacities for each stage. In one example, a three-stage unit can be provided in which the first stage represents about 15 percent of the total capacity, the second stage represents about 30 percent of the total capacity, and the third stage represents about 55 percent of the capacity. In such an example, calculations would be performed for the configurations identified in Table 1 below.

TABLE 1

|  | Stage 1 | Stage 2 | Stage 3 | Leaving DB Temp (° F.) |
|---|---|---|---|---|
| CONFIG 1 | OFF | OFF | OFF | 95.0 |
| CONFIG 2 | ON | OFF | OFF | 89.9 |
| CONFIG 5 | OFF | ON | OFF | 84.8 |
| CONFIG 3 | ON | ON | OFF | 79.7 |
| CONFIG 7 | OFF | OFF | ON | 76.3 |
| CONFIG 4 | ON | OFF | ON | 71.2 |
| CONFIG 6 | OFF | ON | ON | 66.1 |
| CONFIG 8 | ON | ON | ON | 61.0 |

In accordance with the aforementioned calculations, a combined leaving temperature can be derived for each of the eight configurations and the appropriate configuration can then be selected for operation. As shown at Table 1, each configuration represents a unique capacity output that enables the unit to operate between 0 and 100 percent capacity in approximately 15 percent increments.

The various embodiments described above are provided by way of illustration only and should not be construed to limit the claims attached hereto. Those skilled in the art will readily recognize various modifications and changes that may be made without following the example embodiments and applications illustrated and described herein, and without departing from the true spirit and scope of the disclosure.

What is claimed is:

1. A staging control process for an evaporative media cooling system having a plurality of media stages, the staging control process including the steps of:
   a. defining or receiving a leaving air dry bulb temperature setpoint for air exiting the evaporative media cooling system;
   b. calculating an expected media exit dry bulb temperature for each media stage based on a dry bulb temperature and a wet bulb temperature of air entering the media cooling system and based on a measured or assigned condition of the media;
   c. calculating an estimated combined leaving dry bulb temperature for different combinations of activated and deactivated media stages; and
   d. activating the media stage(s) associated with the combination that has an estimated combined leaving dry bulb temperature that is nearest to but less than or equal to the leaving air dry bulb temperature setpoint.

2. The staging control process of claim 1, further comprising the steps of:
   a. defining a plurality of allowed unit staging configurations, each of which representing a different combination of activated and deactivated media stages from all other allowed unit staging configurations.

3. The staging control process of claim 2, wherein:
a. the step of calculating an estimated combined leaving dry bulb temperature for each different combination of activated and deactivated media stages includes calculating an estimated combined leaving dry bulb temperature for each allowed unit staging configuration.

4. The staging control process of claim 2, wherein:
a. the step of defining a plurality of allowed unit staging configurations includes defining:
   i. a first configuration in which a first media stage is activated and a second media stage is deactivated;
   ii. a second configuration in which the second media stage is activated and the first media stage is deactivated;
   iii. a third configuration in which both the first and second media stages are activated.

5. The staging control process of claim 4, wherein:
a. the step of defining a first configuration includes selecting a first media stage that has an output capacity that is about one third of a total output capacity of the system; and
b. the step of defining a second configuration includes selecting a second media stage that has an output capacity that is about two thirds of a total output capacity of the system.

6. The staging control process of claim 1, wherein:
a. wherein the step of calculating an estimated combined leaving dry bulb temperature for each different combination of activated and deactivated media stages includes assigning each deactivated media stage a leaving dry bulb temperature equal to the entering air dry bulb temperature and assigning each activated media stage a leaving dry bulb temperature equal to the expected media exit dry bulb temperature.

7. The staging control process of claim 1, wherein:
a. the step of calculating an estimated combined leaving dry bulb temperature for different combinations of activated and deactivated media stages includes calculating an estimated combined leaving dry bulb temperature for every possible combination of activated and deactivated media stages.

8. The staging control process of claim 1, wherein:
a. the step of activating the media stages includes operating one or more pumps associated with each activated stage.

9. The staging control process of claim 1, wherein:
a. the step of defining or receiving a leaving air dry bulb temperature setpoint for air exiting the evaporative media cooling system includes receiving the setpoint from an electronic controller associated with an air handling system within which the evaporative media system is installed, or defining the setpoint in an electronic controller associated with the evaporative media system.

10. The staging control process of claim 1, wherein:
a. the step of calculating an expected media exit dry bulb temperature based on a measured or assigned condition of the media, includes one of:
   i. using a constant value for the condition of the media;
   ii. calculating a value for the condition of the media based on operating parameters of the evaporative media system;
   iii. using a user input value for the condition of the media; and
   iv. measuring a value for the condition of the media based on operating parameters of the evaporative media system.

11. A staging control process for an evaporative media cooling system having a plurality of media stages, the staging control process including the steps of:
a. defining a plurality of allowed unit staging configurations, each of which represents a combination of activated and deactivated media stages;
b. defining or receiving a leaving air dry bulb temperature setpoint for air exiting the evaporative media cooling system;
c. calculating an estimated combined leaving dry bulb temperature for each allowed unit staging configuration, wherein each deactivated media stage in the configuration is assigned a first leaving dry bulb temperature and wherein each activated media stage is assigned a second dry bulb temperature; and
d. activating the stages associated with the allowed unit staging configuration that has an estimated combined leaving dry bulb temperature that is nearest to but less than or equal to the leaving air dry bulb temperature setpoint.

12. The staging control process of claim 11, further comprising the steps of:
a. each of the allowed unit staging configurations represents a different combination of activated and deactivated media stages from all other allowed unit staging configurations.

13. The staging control process of claim 11, wherein:
a. the step of defining a plurality of allowed unit staging configurations includes defining:
   i. a first configuration in which a first media stage is activated and a second media stage is deactivated;
   ii. a second configuration in which the second media stage is activated and the first media stage is deactivated;
   iii. a third configuration in which both the first and second media stages are activated.

14. The staging control process of claim 11, wherein:
a. the step of defining a plurality of allowed unit staging configurations includes defining configurations based on activating and deactivating different combinations of a first media stage, a second media stage, and a third media stage.

15. The staging control process of claim 14, wherein
a. the step of defining a plurality of allowed unit staging configurations includes selecting a first media stage that has an output capacity that is about 15 percent of a total output capacity of the system, selecting a second media stage that has an output capacity that is about 30 percent of the total output capacity of the system, and selecting a second media stage that has an output capacity that is about 55 percent of the total output capacity of the system.

16. The staging control process of claim 11, wherein:
a. the step of activating the media stages includes activating a pump associated with each activated stage.

17. A control system for an evaporative media cooling system comprising a plurality of media stages, the control system comprising:
a. a controller having a processor and a non-transient storage medium or memory configured to selectively activate and deactivate each media stage;
b. the controller being further configured to implement a staging control process including the steps of:

i. defining or receiving a leaving air dry bulb temperature setpoint for air exiting the evaporative media cooling system;

ii. calculating an expected media exit dry bulb temperature for each media stage based on a dry bulb temperature and a wet bulb temperature of air entering the media cooling system and based on a measured or assigned condition of the media;

iii. calculating an estimated combined leaving dry bulb temperature for different combinations of activated and deactivated media stages; and iv. activating the media stage(s) associated with the combination that has an estimated combined leaving dry bulb temperature that is nearest to but less than or equal to the leaving air dry bulb temperature setpoint.

18. The control system of claim 17, wherein:

a. the controller is an electronic controller that is configured to generate an output signal to one or more fluid pumps associated with the media stages.

19. The control system of claim 17, wherein:

a. the controller is configured to implement the step of calculating an expected media exit dry bulb temperature based on a measured or assigned condition of the media by implementing one of:
 i. using a constant value for the condition of the media;
 ii. calculating a value for the condition of the media based on operating parameters of the evaporative media system;
 iii. using a user input value for the condition of the media; and
 iv. measuring a value for the condition of the media based on operating parameters of the evaporative media system.

20. The control system of claim 17, wherein:

a. the step of defining or receiving a leaving air dry bulb temperature setpoint for air exiting the evaporative media cooling system includes receiving the setpoint from an second controller associated with an air handling system within which the evaporative media system is installed.

\* \* \* \* \*